(12) United States Patent
Roteliuk et al.

(10) Patent No.: US 7,785,263 B2
(45) Date of Patent: Aug. 31, 2010

(54) PRESSURE-BASED SYSTEM AND METHOD FOR DETERMINING CARDIAC STROKE VOLUME

(75) Inventors: Luchy Roteliuk, Lake Forest, CA (US); Russell McKown, Richardson, TX (US); Doug Meyer, Jr., Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 117 days.

(21) Appl. No.: 11/684,525

(22) Filed: Mar. 9, 2007

(65) Prior Publication Data

US 2007/0149884 A1    Jun. 28, 2007

Related U.S. Application Data

(62) Division of application No. 10/728,705, filed on Dec. 5, 2003, now Pat. No. 7,220,230.

(51) Int. Cl.
*A61B 5/021* (2006.01)
(52) U.S. Cl. .................................. 600/485
(58) Field of Classification Search .......... 600/481–507
See application file for complete search history.

(56) References Cited

U.S. PATENT DOCUMENTS

| | | | |
|---|---|---|---|
| 4,236,527 A | 12/1980 | Newbower et al. | |
| 4,429,701 A | 2/1984 | Goor et al. | |
| 4,507,974 A | 4/1985 | Yelderman | |
| 4,535,774 A | 8/1985 | Olson | |
| 4,562,843 A | 1/1986 | Djordjevich et al. | |
| 4,595,015 A | 6/1986 | Jansen et al. | |
| 4,798,211 A | 1/1989 | Goor et al. | |
| 4,834,107 A | 5/1989 | Warner | |
| 5,101,828 A | 4/1992 | Welkowitz et al. | |

(Continued)

FOREIGN PATENT DOCUMENTS

EP         393 228 A1     10/1990

(Continued)

OTHER PUBLICATIONS

Antonutto, G.; Girardos, M.; Tuniz, D.; di Prampero, P.E.; "Noninvasive assessment of cardiac output from arterial pressure profiles during exercise"; European Journal of Applied Physiology, 72 (1995), 18-24.

(Continued)

*Primary Examiner*—Scott M Getzow
(74) *Attorney, Agent, or Firm*—Michael L. Crapenhoft

(57) ABSTRACT

Cardiac stroke volume (SV) of a subject is estimated as a function of a value derived from a measured arterial pressure waveform. The value may be the standard deviation, or a function of the difference between maximum and minimum pressure values, or a function of either the maximum value of the first time derivative or the absolute value of the minimum of the first time derivative of the pressure waveform, or both, or a function of the magnitude of one or more spectral components of the pressure waveform at a frequency corresponding to the heart rate. Cardiac output is then estimated as the product of the subject's heart rate and SV, scaled by a calibration constant. Arterial pressure may be measured invasively or non-invasively.

12 Claims, 2 Drawing Sheets

U.S. PATENT DOCUMENTS

| | | | |
|---|---|---|---|
| 5,146,414 A | 9/1992 | McKown et al. | |
| 5,178,151 A | 1/1993 | Sackner et al. | |
| 5,183,051 A | 2/1993 | Kraidin et al. | |
| 5,199,438 A | 4/1993 | Pearlman | |
| 5,211,177 A | 5/1993 | Chesney et al. | |
| 5,241,966 A | 9/1993 | Finkelstein et al. | |
| 5,265,011 A | 11/1993 | O'Rourke | |
| 5,265,615 A * | 11/1993 | Frank et al. | 600/485 |
| 5,316,004 A | 5/1994 | Chesney et al. | |
| 5,390,679 A | 2/1995 | Martin | |
| 5,400,793 A | 3/1995 | Wesseling | |
| 5,423,323 A | 6/1995 | Orth | |
| 5,526,817 A | 6/1996 | Pfeiffer et al. | |
| 5,533,511 A | 7/1996 | Kaspari et al. | |
| 5,535,753 A | 7/1996 | Petrucelli et al. | |
| 5,584,298 A | 12/1996 | Kabal | |
| 5,634,467 A | 6/1997 | Nevo | |
| 5,638,823 A | 6/1997 | Akay et al. | |
| 5,647,369 A | 7/1997 | Petrucelli et al. | |
| 5,687,733 A | 11/1997 | McKown | |
| 5,730,138 A | 3/1998 | Wang | |
| 5,743,268 A | 4/1998 | Kabal et al. | |
| 5,746,698 A | 5/1998 | Bos et al. | |
| 5,769,062 A | 6/1998 | Antao | |
| 5,797,395 A | 8/1998 | Martin | |
| 5,830,131 A | 11/1998 | Caro et al. | |
| 5,865,758 A | 2/1999 | Louzianine | |
| 5,876,347 A | 3/1999 | Chesney et al. | |
| 5,913,826 A | 6/1999 | Blank | |
| 6,004,274 A | 12/1999 | Nolan et al. | |
| 6,010,457 A | 1/2000 | O'Rourke | |
| 6,017,313 A | 1/2000 | Bratteli et al. | |
| 6,048,318 A | 4/2000 | Chesney et al. | |
| 6,071,244 A | 6/2000 | Band et al. | |
| 6,090,047 A | 7/2000 | Kass et al. | |
| 6,117,087 A | 9/2000 | Kamm et al. | |
| 6,141,590 A | 10/2000 | Renirie et al. | |
| 6,165,130 A | 12/2000 | Chio | |
| 6,216,094 B1 | 4/2001 | Fox Linton et al. | |
| 6,224,585 B1 | 5/2001 | Pfeiffer | |
| 6,228,033 B1 | 5/2001 | Kööbi et al. | |
| 6,231,498 B1 | 5/2001 | Pfeiffer et al. | |
| 6,270,461 B1 | 8/2001 | Chio | |
| 6,290,651 B1 | 9/2001 | Chesney et al. | |
| 6,315,735 B1 | 11/2001 | Joeken et al. | |
| 6,348,038 B1 | 2/2002 | Band et al. | |
| 6,394,958 B1 | 5/2002 | Bratteli et al. | |
| 6,471,655 B1 | 10/2002 | Baura | |
| 6,485,431 B1 | 11/2002 | Campbell | |
| 6,514,211 B1 | 2/2003 | Baura | |
| 6,554,774 B1 | 4/2003 | Miele | |
| 6,676,608 B1 | 1/2004 | Keren | |
| 7,220,230 B2 | 5/2007 | Roteliuk et al. | |
| 2002/0022785 A1 | 2/2002 | Romano | |
| 2002/0052553 A1 | 5/2002 | Shalman et al. | |
| 2003/0060722 A1 | 3/2003 | Pfeiffer et al. | |
| 2003/0167010 A1 | 9/2003 | Pinsky | |
| 2003/0191400 A1 | 10/2003 | Shalman et al. | |
| 2004/0087863 A1 | 5/2004 | Eide | |
| 2004/0158163 A1 | 8/2004 | Cohen et al. | |
| 2007/0191724 A1 | 8/2007 | Hirsh | |

FOREIGN PATENT DOCUMENTS

| | | |
|---|---|---|
| EP | 420 085 A2 | 4/1991 |
| EP | 448 979 A1 | 10/1991 |
| EP | 564 492 B1 | 10/1993 |
| EP | 569 506 B1 | 11/1993 |
| EP | 642 760 A1 | 3/1995 |
| EP | 947 160 A1 | 10/1999 |
| EP | 947 941 A2 | 10/1999 |
| EP | 1236435 | 9/2002 |
| WO | WO 90/03145 | 4/1990 |
| WO | WO 90/11042 | 10/1990 |
| WO | WO 92/06633 | 4/1992 |
| WO | WO 92/11804 | 7/1992 |
| WO | WO 92/12669 | 8/1992 |
| WO | WO 94/14372 | 7/1994 |
| WO | WO 94/22363 | 10/1994 |
| WO | WO 95/16391 | 6/1995 |
| WO | WO 97/24982 | 7/1997 |
| WO | WO 98/19594 | 5/1998 |
| WO | WO 99/02086 | 1/1999 |
| WO | WO 00/64339 | 11/2000 |

OTHER PUBLICATIONS

Fagard, R. and Conway, 3 (1990); "Measurement of cardiac output: Fick principle using catheterization"; Eur. Heart J. 11, Suppl. I., pp. 1-5.

Ganz, W. and Swan, H.J.C. (1972); "Measurement of blood flow by thermodilution"; Am. J. Cardiol. 29, pp. 241-246.

Goedje, O.; Hoeke, K.; Lichtwark-Aschoff, M.; Faltchauser, A.; Lamm, P.; Reichart, B.; "Continuous cardiac output by femoral arterial thermodilution calibrated pulse contour analysis: Comparison with pulmonary arterial thermodilution"; Critical Care Medicine, 27 (1999), 2407-2412.

Gratz, I; Kraidin, J.; Jacobi, A.G.; deCastro, N.G.; Spagna, P.; Larijani, G.E.; "Continuous noninvasive cardiac output as estimated from the pulse contour curve"; Journal of Clinical Monitoring, 8 (1992), 20-27.

Harms, M.P.M.; Wesseling, K.H.; Pott, F., et al. (1999); "Continuous stroke volume monitoring by modelling flow from non invasive measurement of arterial pressure in humans under orthostatic stress"; Clin. Sci. 97, pp. 291-301.

Houtman, S.; Oeseburg, B. And Hopman, M.T.E. (1999); "Non invasive cardiac output assessment during moderate exercise: pulse contour compared with C02 rebreathing"; Clin. Physiol. 19, pp. 230-237.

Irlbeck, M.; Forst, H.; Briegel, J.; Haller, M.; Peter, K.; "Die kontinuierliche Messung des Herzzeitvolumens mit der Pulskonturanalyse; Der Anaesthesist"; 44 (1995), 493-500 German? Abstract.

Jansen, J.R.; Wesseling, K.H.; Settels, J.J.; Schreuder, J.J.; "Continuous cardiac output monitoring by pulse contour during cardiac surgery"; European Heart Journal, 11 (1990), 26-32.

Jansen, J.R.C.; Schreuder, J.J.; Mulier, J.P.; Smith, N.T.; Settels, J.J. And Wesseling, K.H.; "A comparison of cardiac output derived from the arterial pressure wave against thermodilution in cardiac surgery patients"; British Journal of Anaesthesia, 87 (2) (2001), 212-22.

Jellema, W.T.; Wesseling, K.H.; Groeneveld, A.B.J; Stoutenbeek, C.P.; Thjis, L.G. and van Lieshout, J.J. (1999); "Continuous cardiac output in septic shock by simulating a model of the thermodilution"; Anesthesiology 90, pp. 1317-1328.

Jellema, W.T.; Imholz, B.P.M.; van Goudoever, J.; Wesseling, K.H. and van Lieshout, J.J. (1996); "Finger arterial versus intrabrachial pressure and continuous cardiac output during head up tilt testing in healthy subjects"; Clin. Sci. 91, pp. 193-200.

Langewouters, G.J.; Wesseling, K.H. And Goedhard, W.J.A. (1984); "The static elastic properties of 45 human thoracic and 20 abdominal aortas in vitro and the parameters of a new model"; J. Biomech. 17, pp. 425-435.

McKay, W.P.; Gregson, P.H.; McKay, B.W.; Militzer, J.; "Sternal acceleration ballistocardiography and arterial pressure wave analysis to determine stroke volume"; Clinical and Investigative Medicine, 22 (1999), 4-14.

Martin, J.F.; Volfson, L.B.; Kirzon-Zolin, V.V.; Schukin, V.G.; "Application of pattern recognition and image classification techniques to determine continuous cardiac output from the arterial pressure waveform"; IEEE Transactions on Biomedical Electronics, 41 (1994), 913-920.

Romano, Salvatore M.; Pistolesi, Massimo; "Assessment of cardiac output from systemic arterial pressure in humans"; Crit Care Med 2002 vol. 30, No. 8, pp. 1834-1841.

Sprangers, R.L.; Wesseling, K.H.; Imholz, A.L.; Imholz, B.P. and Wieling, W. (1991); "Initial blood pressure fall on stand up and exercise explained by changes in total peripheral resistance"; J. Appl. Physiol. 70, pp. 523-530.

Stok, W.J.; Baisch, F.; Hillebrecht, A.; Schulz, H. And Karemaker, J.M. (1993); "Noninvasive cardiac output measurement by arterial pulse analysis compared to inert gas rebreathing"; J. Appl. Physiol. 74, pp. 2687-2693.

Stok, W.J.; Stringer, R.C.O. and Karemaker, J.M. (1999); "Noninvasive cardiac output measurement in orthostasis: pulse contour analysis compared with acetylene rebreathing"; J. Appl. Physiol. 87, pp. 2266-2273.

Wesseling, K.H.; De Wit, B.; Weber, J.A.P. And Smith, N.T. (1983); "A simple device for the continuous measurement of cardiac output. Its model basis and experimental verification"; Adv. Cardiol. Phys. 5, Suppl. II, pp. 16 52.

Wesseling, K.H.; Jansen, J.R.C.; Settels, J.J. and Schreuder, J.J. (1993); "Computation of aortic flow from pressure in humans using a nonlinear, three element model"; J. Appl. Physiol. 74, pp. 2566-2573.

Examination Report for EP05771463.6, dated Mar. 10, 2009.

Chinese Patent Office, First Office Action, Nov. 2, 2007.

\* cited by examiner

PRESSURE-BASED SYSTEM AND METHOD FOR DETERMINING CARDIAC STROKE VOLUME

RELATED APPLICATIONS

The present application is a divisional of U.S. Ser. No. 10/728,705 filed on Dec. 5, 2003 now U.S. Pat. No. 7,220,230 entitled Pressure-Based System and Method for Determining Cardiac Stroke Volume which is incorporated herein by reference in its entirety.

BACKGROUND OF THE INVENTION

1. Field of the Invention

This invention relates to a method for determining the stroke volume (SV) and, hence, any other SV-related value such as cardiac output of a human or animal subject, as well as to a system that implements the method.

2. Background Art

Cardiac output (CO) is an important indicator not only for diagnosis of disease, but also for "real-time" monitoring of the condition of both human and animal subjects, including patients. Few hospitals are therefore without some form of conventional equipment to monitor cardiac output.

One basis for almost all common CO-measurement systems is the well-known formula CO=HR·SV, where SV is the stroke volume and HR is the heart rate. SV is usually measured in liters and HR is usually measured in beats per minute. This formula simply expresses that the amount of blood the heart pumps out in a minute is equal to the amount it pumps out on every beat (stroke) times the number of beats (strokes) per minute.

Since HR is easy to measure using any of a wide variety of instruments, the calculation of CO usually depends on some technique for estimating SV. Many suitable techniques—both invasive and non-invasive, as well as those that combine both—are in use and even more have been proposed in the literature.

One invasive way to determine cardiac output (or, equivalently, SV) is to mount some flow-measuring device on a catheter, and then to place the catheter into the subject and to maneuver it so that the device is in or near the subject's heart. Some of such devices inject either a bolus of material or energy (usually heat) at an upstream position, such as in the right atrium, and determine flow based on the characteristics of the injected material or energy at a downstream position, such as in the pulmonary artery. Patents that disclose implementations of such invasive techniques (in particular, thermodilution) include:

U.S. Pat. No. 4,236,527 (Newbower et al., 2 Dec. 1980);
U.S. Pat. No. 4,507,974 (Yelderman, 2 Apr. 1985);
U.S. Pat. No. 5,146,414 (McKown, et al., 8 Sep. 1992); and
U.S. Pat. No. 5,687,733 (McKown, et al., 18 Nov. 1997).

Still other invasive devices are based on the known Fick technique, according to which CO is calculated as a function of oxygenation of arterial and mixed venous blood. In most cases, oxygenation is sensed using right-heart catheterization. There have, however, also been proposals for systems that measure arterial and venous oxygenation non-invasively, in particular, using multiple wavelengths of light, but to date they have not been accurate enough to allow for satisfactory CO measurement on actual patients.

Invasive techniques have some disadvantages, the main one of which is of course that catheterization of the heart is more dramatic to the patient, especially considering that the subjects (especially intensive care patients) on which it is performed are often already in the hospital because of some actually or potentially serious condition. Invasive methods also have less obvious disadvantages: Some techniques such as thermodilution rely on assumptions, such as uniform dispersion of the injected heat, that affect the accuracy of the measurements depending on how well they are fulfilled. Moreover, the very introduction of an instrument into the blood flow may affect the value (for example, flow rate) that the instrument measures.

There has therefore been a long-standing need for some way of determining CO that is both non-invasive—or at least as minimally invasive as possible—and accurate. One blood characteristic that has proven particularly promising for accurately determining CO non-invasively is blood pressure.

Most known blood-pressure-based systems rely on the so-called pulse contour method (PCM), which calculates as estimate of GCO from characteristics of the beat-to-beat pressure waveform. In the PCM, "Windkessel" (German for "air chamber") parameters (characteristic impedance of the aorta, compliance, and total peripheral resistance) are used to construct a linear or non-linear, hemodynamic model of the aorta. In essence, blood flow is analogized to a flow of electrical current in a circuit in which an impedance is in series with a parallel-connected resistance and capacitance (compliance). The three required parameters of the model are usually determined either empirically, through a complex calibration process, or from compiled "anthropometric" data, that is, data about the age, sex, height, weight, etc., of other patients or test subjects. U.S. Pat. No. 5,400,793 (Wesseling, 28 Mar. 1995) and U.S. Pat. No. 5,535,753 (Petrucelli, et al., 16 Jul. 1996) are representative of systems that rely on a Windkessel circuit model to determine CO.

PCM-based systems can monitor CO more or less continuously, with no need for a catheter to be left in the patient. Indeed, some PCM systems operate using blood pressure measurements taken using a finger cuff. One drawback of PCM, however, is that it is no more accurate than the rather simple, three-parameter model from which it is derived; in general, a model of a much higher order would be needed to faithfully account for other phenomena, such as the complex pattern of pressure wave reflections due to multiple impedance mismatches caused by, for example, arterial branching. Because the accuracy of the basic model is usually not good enough, many improvements have been proposed, with varying degrees of complexity.

The "Method and apparatus for measuring cardiac output" disclosed by Salvatore Romano in U.S. Published Patent Application 20020022785 A1 represents a different attempt to improve upon PCM techniques by estimating SV, either invasively or non-invasively, as a function of the ratio between the area under the entire pressure curve and a linear combination of various components of impedance. In attempting to account for pressure reflections, the Romano system relies not only on accurate estimates of inherently noisy derivatives of the pressure function, but also on a series of empirically determined, numerical adjustments to a mean pressure value.

What is needed is a system and method of operation for estimating CO that is robust, simple, and accurate and that does not require anthropometric values or repeated calibrations. This invention meets this need.

SUMMARY OF THE INVENTION

A parameter proportional to the cardiac stroke volume (SV) of a patient is determined by sensing an input signal that either directly indicates or is proportional to arterial blood pressure. The sensor used to sense the input signal may be either invasive or non-invasive. The standard deviation of the input signal is then calculated over a measurement interval and an estimate of SV is then calculated as a function of the standard deviation of the input signal. SV may be also computed as the product of the standard deviation and a calibration factor. In an exemplifying processing system that implements the method, one or more computer-executable software modules are included for carrying out the various calculations.

Any cardiac value derived from SV may also use the invention to determine an SV estimate to be used for calculating the value. For example, the method according to the invention may be used to calculate an estimate of cardiac output (CO). In such an application of the invention, any known mechanism (for example, a hardware monitor and/or software algorithm) is used to measure the patient's heart rate (HR). The current cardiac output of the patient is then estimated, for example, by calculating the product of HR and the standard deviation and scaling the product by a calibration constant.

In CO applications of the invention, the calibration constant may be determined using different techniques, both invasive and non-invasive. To calculate the calibration constant, a calibration cardiac output value is measured and the calibration constant is approved as the quotient between a calibration cardiac output estimate and the product of the heart rate and the standard deviation.

The measurement interval may extend over more than one cardiac cycle, for example, to cover a time window that is multiple cardiac cycles wide. A single standard deviation value of the input signal may be calculated over the whole interval, or component standard deviation values may be calculated and then averaged (using the mean, median, etc.) for each of a plurality of sub-intervals to form a final composite standard deviation value that can be used in calculating the estimate of the cardiac stroke volume.

Various optimizations may be included in different embodiments of the invention. For example, for each of a plurality of cardiac cycles, a mean pressure value can be calculated and the measurement interval can then be adjusted as a function of change in the mean pressure value.

If needed, for example, to remove the effect of potential drift in mean pressure over the measurement interval(s), the input signal may be high-pass filtered before standard deviation is calculated.

Standard deviation may be calculated in different ways, having different degrees of statistical accuracy. For example, the input signal may be discretized over the measurement interval, and then a standard algorithm may be applied to determine an estimate of standard deviation from the sample values. As an alternative, standard deviation may be approximated as a function of the difference between the maximum and minimum values.

DETAILED DESCRIPTION

Introduction

Figure 1:
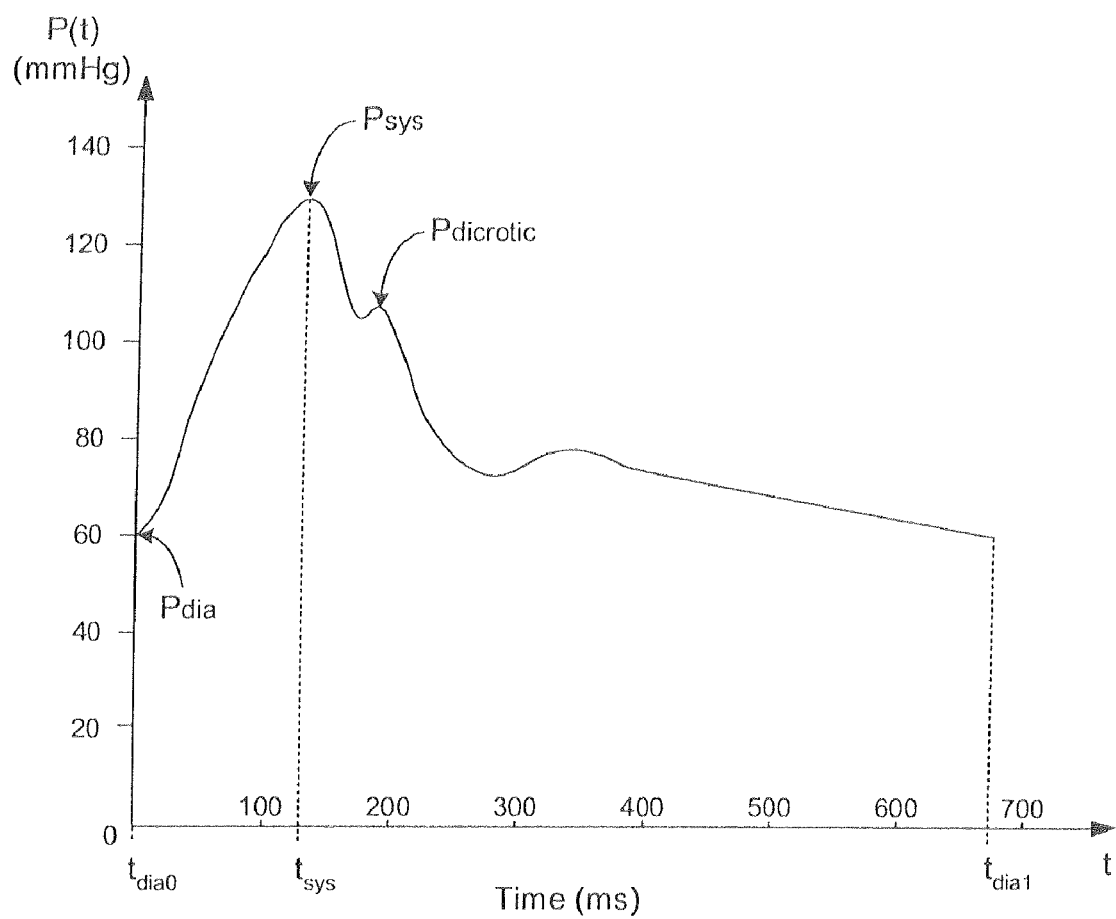
FIG. 1 is an illustrative example of a complex blood pressure curve over one beat-to-beat heart cycle

In broadest terms, the invention involves the determination of a cardiac value such as stroke volume (SV), and/or a value derived from SV such as cardiac output (CO), using information extracted from an arterial pressure waveform, or from a waveform that is proportional to arterial pressure, which may be measured with an invasive, non-invasive, or "minimally invasive" instrument or combination of instruments The organization of this description is: First, the theoretical basis of the invention is discussed. This is followed by an explanation of the main steps of a method to use the theory, then a description of a system that implements the method.

The invention may be used to advantage with any type of subject, whether human or animal. Because it is anticipated that the most common use of the invention will be on humans in a diagnostic setting, the invention is described below primarily in use with a "patient." This is by way of example only, however—it is intended that the term "patient" should encompass all subjects, both human and animal, regardless of setting.

Theoretical Basis of the Invention

As mentioned above, the principle formula for calculating cardiac output (CO) is CO=SV·HR, where SV is stroke volume and HR is heart rate. Given HR, the problem then remains how to determine SV. Based on the observation that the pulsatility of a pressure waveform is created by the cardiac stroke volume into the arterial tree, inventors have discovered that one particularly elegant solution to the problem is to estimate SV to be proportional to the standard deviation of the arterial pressure waveform P(t), or of some other signal that itself is proportional to P(t). Thus, according to this aspect of the invention, $$SV = K \cdot \sigma_P$$

from which follows that $$CO = K \cdot \sigma_P \cdot HR$$

where K is a constant and $\sigma_P$ is the standard deviation of P(t) (or of some other signal proportional to P(t)) taken over some time interval. Other quickly computed functions of P(t) that provide values proportional to SV are also discussed below.

Steps for Determining CO

As mentioned above, the invention may be used to determine SV, and hence any other cardiac value that is a function of SV. It is anticipated that the most common use of the invention will be to determine CO, so the exemplary embodiments of the invention are described below primarily with respect to this application. Since the invention generates an estimate of SV, however those skilled in the art of medical systems will know how to use the estimated SV value to derive still other cardiac values.

The first step in the method for measuring CO is to acquire a representation of either the arterial pressure waveform P(t) or of some waveform that is proportional to P(t). This may be a direct measurement of arterial pressure, or a measurement of some other parameter that is proportional to arterial pressure. For example, a plethysmographic technique, for example, using a finger cuff, will produce a signal that is proportional to arterial blood pressure; this signal can then be scaled to convert to an estimate of blood pressure. For the sake of succinctness, the method for determining SV is discussed below with reference to the arterial pressure waveform P(t), but one should keep in mind that the disclosed method steps may easily be adjusted to use another, proportional waveform, simply by applying the proper scaling, such as the scaling provided by a calibration factor K described below.

FIG. 1 illustrates an example of the waveform P(t) of arterial pressure taken over a single heart cycle, here, from the point of diastolic pressure $P_{dia}$ at time $t_{dia0}$, through the time $t_{sys}$ of systolic pressure $P_{sys}$, to a time $t_{dia1}$ at which the blood pressure once again reaches $P_{dia}$.

According to the invention, P(t), or any signal that is proportional to P(t), may be measured at any point in the arterial tree, either invasively or non-invasively. If invasive instruments are used, in particular, catheter-mounted pressure transducers, then any artery may be used as a measurement point. Placement of non-invasive transducers will typically be dictated by the instruments themselves—the placement of finger cuffs, upper arm pressure cuffs, and earlobe clamps should be obvious. Regardless of the instrument, it will ultimately produce, or cause to be produced, an electric signal corresponding (for example, proportional) to P(t).

As is well known, analog signals such as P(t) can be digitized into a sequence of digital values using any standard analog-to-digital converter (ADC). In other words, P(t), $t0 \leq t \leq tf$, can be converted, using known methods and circuitry, into the digital form P(k), k=0, (n−1), where t0 and tf are initial and final times, respectively, of the measurement interval and n is the number of samples of P(t) to be included in the calculations, distributed usually evenly over the measurement interval.

The next step of the procedure is to calculate the standard deviation of P(k), that is, $\sigma_P$, or some value that has a known relationship to the standard deviation (see below). One way to calculate $\sigma_P$ is to use the well-known algorithm for calculating the standard deviation of a discretized function. Thus:

$$\sigma_P^2 = \frac{1}{n-1} \sum_{k=1}^{n} [P(k) - P_{avg}]^2 \quad \text{(Equation 1)}$$

where $P_{avg}$ is the mean pressure value, that is:

$$P_{avg} = \frac{1}{n} \sum_{k=1}^{n} P(k) \quad \text{(Equation 2)}$$

Of course, to get $\sigma_P$ the system simply takes the square root of $\sigma_P^2$.

The analog measurement interval, that is, the time window [t0, tf], and thus the discrete sampling interval k=1, n, over which a CO estimate is calculated should be small enough so that it does not encompass substantial shifts in the mean pressure $P_{avg}$. Also, one could filter out low frequency variations such as respiration using a high pass filter, which would also help remove the effect of any drift in mean arterial pressure during the time window. For the sake of providing more stable and reliable readings, however, is it best to let the time window for each CO estimate extend longer than one cardiac cycle. Preferably, the measurement interval (time window) should be a plurality of cardiac cycles, that is, beginning and ending at the same point in different cardiac cycles; this ensures that the mean pressure value used in the calculations of $\sigma$ will use a mean pressure value $P_{avg}$ that is not skewed because of incomplete measurement of a cycle. Since the information is available to any embodiment of the invention that uses $P_{avg}$ (for example, in the calculation of $\sigma_P$), it may be useful in some implementations to always display the current mean blood pressure and/or trend to the user.

Larger sampling windows have the advantage that the effect of perturbations such as those caused by reflections will usually be reduced, since they will be tend to "cancel out" in the calculations of mean pressure and standard deviation. An appropriate time window can be determined using normal experimental and clinical methods. Note that it would be possible for the time window to coincide with a single heart cycle, in which case mean pressure shift will not be of concern.

As a check, the system according to the invention could also, as a separate background operation, compute the mean pressure over each cardiac cycle. If the mean cycle-to-cycle pressure shows any absolute or proportional drift greater than some threshold value, a warning signal could be generated such that the currently computed CO estimate may be considered less reliable or discarded altogether.

It would be also possible to adjust the time window [t0, tf] according to drift in $P_{avg}$. For example, if $P_{avg}$ over a given time window differs absolutely or proportionately by more than a threshold amount from the $P_{avg}$ of the previous time window, then the time window could be reduced; stability of $P_{avg}$ could then be used to indicate that the time window can be expanded. The time window could also be expanded and contracted based on noise sources, or on a measure of SNR or of SNR variation. In a preferred embodiment, limits are placed on how much the time window is allowed to expand or contract; and an indication of the time interval is displayed to the user.

It is not necessary for the time window to start at any particular point in the cardiac cycle. Thus, $t_0$ need not be the same as $t_{dia0}$, although this may be a convenient choice in many implementations. This means that the beginning and end of each measurement interval (that is, t0 and tf), each yielding a CO estimate, may be triggered on almost any characteristic of the cardiac cycle, such as at times $t_{dia0}$ or $t_{sys}$, or on non-pressure characteristics such as R waves, etc.

Rather than calculate a single $\sigma_P$ value from a multi-cycle measurement as in Equation 1 it would also be possible to calculate several $\sigma_P$, for example, one for each of a plurality of intervals, and then to average them (by taking the mean, median, etc.) to compute a composite $\sigma_P$ for use in the formulas. The inventors have, moreover, discovered other alternatives for computing a pulsatility variable similar to the standard deviation $\sigma_P$ of the arterial blood pressure.

The inventors have observed that other values may be derived from the pressure waveform P(t) that either provide an approximation of up, or that also are proportional to SV, or both. As one example, the inventors have observed that the difference between the maximum and minimum measured pressures, taken over the time window, is a pulsatility measurement that may be substituted for direct calculation of $\sigma_P$ using the standard formulas given above as Equations 1 and 2. Let max[P(k)] and min[P(k)] be the maximum and minimum values, respectively, of the sampled pressure over the measurement interval. The standard deviation is approximately equal to one-third times the difference of these two values:

$$\sigma_P \approx \{\max[P(k)] - \min[P(k)]\}/3$$

Although probably less accurate than calculation of up using Equations 1 and 2, this "rough" $\sigma_P$ approximation has the advantage of simplicity, requiring no sampling of P(t) at all. Indeed, given an input signal indicating heart rate (HR), a system to compute $\{\max[P(k)] - \min[P(k)]\}/3$ and, from it, SV and/or CO (or some other function of SV) could be implemented completely in hardware, even all-analog circuitry, using known circuit design techniques. This would allow development of very inexpensive, easily manufactured and physically robust CO monitors for use in areas or applications that have only minimal facilities and resources.

Of course, it is not necessary to have a separate calculation relating max[P(k)] and min[P(k)] to $\sigma_P$, and then to use up to calculate SV. This is described here by way of illustration only. Rather, given max[P(k)] and min[P(k)], SV can be estimated directly as:

$$SV = k \cdot \{\max[P(k)] - \min[P(k)]\}$$

where k=K/3. (Of course, K can simply be adjusted to account for the factor ⅓)

As another alternative, the inventors have observed that the maximum or absolute value of the minimum of the first derivative of the P(t) with respect to time is generally proportional to $\sigma_P$ and to SV. Thus:

$$SV = K \cdot \max\left(\frac{dP(t)}{dt}\right) \quad \text{or} \quad SV = K \cdot \left|\min\left(\frac{dP(t)}{dt}\right)\right|$$

It would also be possible to use the average or these first derivatives instead of using only the one or the other. Given P(k), the derivatives may be determined using any known numerical method; note that the points of interest on the pressure waveform are the points of inflection, that is, the points at which the second time derivative of P(t) is zero. The time interval over which these derivatives is evaluated may be the entire cardiac cycle. It will generally suffice, however, to evaluate P(t) between the beginning of the cardiac and the first dicrotic point, shown as $P_{dicrotic}$ in FIG. 1, since the maximum positive slope will usually occur about half way between the diastolic and systolic points, that is, $P_{dia}$ and $P_{sys}$ and the greatest negative slope will generally occur about half way between the systolic and first dicrotic points, that is, $P_{sys}$ and $P_{dicrotic}$. Examining only these portions of P(t) will eliminate the possibility that spurious values will be used from after the time of $P_{dicrotic}$.

As yet another alternative, a standard software or hardware module could be used to compute the Fourier transform of the measured pressure signal P(t) over each cardiac cycle, or over a multiple of cycles. The quantity defined by the magnitude of the Fourier transform component, H1, at the primary frequency component, i.e., the frequency corresponding to the "heart rate," divided by the mean arterial pressure $P_{avg}$, that is, H1/$P_{avg}$, will be proportional to SV. Instead of H1, the magnitude of the Fourier component H2 corresponding to twice the heart rate, that is, the first harmonic frequency component, cold be used instead; thus, H2/$P_{avg}$ will also be proportional to SV.

In order to calculate CO, the heart rate HR (or some signal from which HR can be derived) is needed. Any of the many known instruments for measuring HR may be used. If the beginning and end times for each P(t) interval are triggered by an electrocardiogram signal, for example, then the same signal may be used to calculate HR. The measured pressure wave P(t) (in practice, P(k)) may itself be used to derive HR, for example, using standard Fast Fourier transformation or derivative analysis.

Before finally arriving at a value for CO, it is also necessary to determine a value for the calibration constant K. One way to do this is as any pre-determined function of P(t); thus, K=K(P(t)). In this case no independent CO technique is necessary.

Another way to do this is to use any known, independent GO technique to determine this relationship, whether invasive, for example, thermodilution, or non-invasive, for example, trans-esophageal echocardiography (TEE) or bio-impedance measurement. The invention provides continuous trending of CO between intermittent measurements such as TD or TEE. Using the chosen independent method, a value $CO_{cal}$ is determined, so that K will be:

$$K = CO_{cal}/(V \cdot HR)$$

where V is the chosen value proportional to SV, for example:
V=$\sigma_P$; or
V=max[P(k)]−min[P(k)]; or
V=maximum or absolute value of the minimum of the first derivative of the P(t); or
V=H1/$P_{avg}$ or H2/$P_{avg}$ Even if an invasive technique such as catheterization is used to determine K, it will usually not be necessary to leave the catheter in the patient during the subsequent CO-monitoring session. Moreover, even when using catheter-based calibration technique to determine K, it is not necessary according to the invention for the measurement to be taken in or near the heart; rather, the calibration measurement could be made in the femoral artery. As such, even where an invasive technique is used to determine the calibration constant K, the invention as a whole is still minimally invasive in that any catheterization may be peripheral and temporary.

Figure 2:
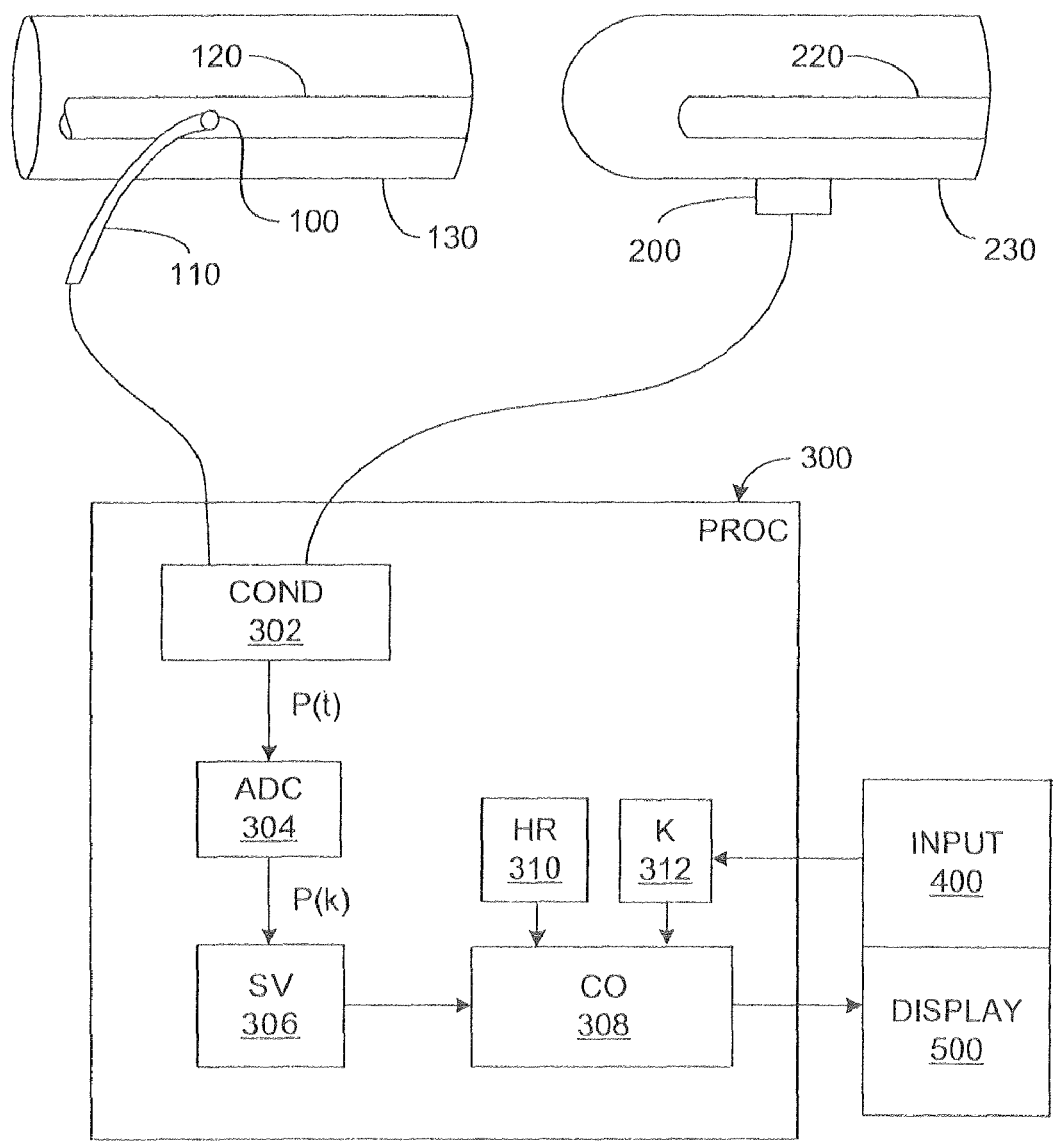
FIG. 2 is a block diagram showing the main components of a system according to the invention.

As is mentioned above, rather than measure arterial blood pressure directly, any other input signal may be used that is proportional to blood pressure. This means that calibration may be done at any or all of several points in the calculations. For example, if some signal other than arterial blood pressure itself is used as input, then it may be calibrated to blood pressure before its values are used to calculate standard deviation, or afterwards, in which case either the resulting standard deviation value can be scaled, or the resulting SV value can be calibrated (for example, by setting K properly), or some final function of SV (such as CO) can be scaled. In short, the fact that the invention may in some cases use a different input signal than a direct measurement of arterial blood pressure does not limit its ability to generate an accurate SV estimate System Components FIG. 2 shows the main components of a system that implements the method described above for sensing pressure and calculating CO. As is mentioned above, pressure, or some other input signal proportional to pressure, may be sensed in either or, indeed, both, of two ways: invasively and non-invasively. Simply because it is anticipated to be the most common implementation of the invention, the system is described as measuring arterial blood pressure (as opposed to some other input signal that is converted to pressure) and generating a CO estimate (as opposed to just SV). Changes to the illustrated system to accommodate other design choices will be obvious to those skilled in the art of medical devices.

FIG. 2 shows both types of pressure sensing for the sake of conciseness; in most practical applications of the invention, either one or several variations will typically be implemented. In invasive applications of the invention, a conventional pressure sensor 100 is mounted on a catheter 110, which is inserted in an artery 120 of a portion 130 of the body of a human or animal patient. Such artery could be an ascending aorta, or pulmonary artery, or, in order to reduce the level of invasiveness, the artery 120 could be peripheral, such as the femoral, radial or brachial artery. In the non-invasive applications of the invention, a conventional pressure sensor 200, such as a photo-plethysmographic blood pressure probe, is mounted externally in any conventional manner, for example using a cuff around a finger 230 or a transducer mounted on the wrist of the patient. FIG. 2 schematically shows both types.

The signals from the sensors 100, 200 are passed via any known connectors as inputs to a processing system 300, which includes one or more processors and other supporting hardware and system software (not shown) usually included to process signals and execute code. The invention may be implemented using a modified, standard, personal computer, or it may be incorporated into a larger, specialized monitoring system. In this invention, the processing system 300 also may include, or is connected to, conditioning circuitry 302 which performs such normal signal processing tasks as amplification, filtering, ranging, etc., as needed, as well as the optional high pass filtering mentioned above. The conditioned, sensed input pressure signal P(t) is then converted to digital form by a conventional analog-to-digital converter ADC 304. As is well understood, the sampling frequency of the ADC 304 should be chosen with regard to the Nyquist criterion so as to avoid aliasing of the pressure signal; this procedure is very well known in the art of digital signal processing. The output from the ADC 304 will be the discrete pressure signal P(k), whose values may be stored in conventional memory circuitry (not shown).

The values P(k) are passed to (usually, accessed from memory by) to an SV-calculation module 306, which is a software component comprising processor-executable code for calculating whichever value V is used to determine SV as explained above. For example, where up is calculated directly, the SV-calculation module 306 will evaluate Equations 1 and 2 above, or equivalent expressions. The calculation module 306 preferably also selects the time window [t0, tf] over which each CO estimate is generated. This may be done as simply as choosing which and how many of the stored, consecutive, discretized P(t) values P(k) are used in each calculation, which is the same as selecting n in the range k=1, . . . , n.

The computer value of SV is then passed to a subsequent CO-calculation module 308, which similarly comprises executable code for evaluate the expression CO=K·$\sigma_P$·HR. Of course, modules 306 and 308 may be combined into a single software component; they are shown separately for the sake of clarity. Of course, the CO-calculation module 308 requires values for HR and K as well:

The patient's current heart rate HR is either calculated from the measured pressure curve P(k) by a corresponding software module 310 (for example, using Fourier or derivative analysis) or is otherwise measured with any conventional hardware device.

The value K will normally be input to module 308 automatically, but can be entered by the operator via a conventional input device 400 such as a keyboard, mouse, etc. This will usually be the same input device(s) used by the processing system 300 for other purposes such as entering data identifying the patient and the specifications of the monitoring session.

The module 308 calculates and estimates CO for each chosen measurement interval. Each estimated CO value is preferably output to any conventional display or printing device 500 for the user to view and monitor. As with the input device 400, the display 500 will typically be the same as is used by the processing system for other purposes.

The invention further relates to a computer program loadable in a computer unit or the processing system 300 in order to execute the method of the invention. Moreover, the various software modules 306, 308, 310, and 312 used to perform the various calculations and perform related method steps according to the invention may also be stored as computer-executable instructions on a computer-readable medium in order to allow the invention to be loaded into and executed by different processing systems.

Other Outputs

The invention is described above in the context of calculating estimates of CO. This is the use of invention that the inventor assumes will be most common, but the invention is not inherently limited to such use. In essence, the invention provides a novel way to calculate stroke volume SV, or any parameter that is a function of (for example, proportional to) SV, not just CO. Consequently, the advantages of the invention will apply to the calculation of any value derived from SV. For example, the end diastolic volume (EDV) and the ejection fraction (EF) are related as EF=SV/EDV, which expresses the intuitive relationship that the pumping efficiency (EF) of the heart is the ratio between how much blood the heart pumps out on every beat (contraction) and how much blood is in the heart chamber just before the beat. Inversely, EDV=SV/EF. If an estimate for either EDV or EF is determined in some other known manner, then the invention could be used to provide SV, and thus an estimate of the other of EDV or EF.

What is claimed is:

1. A method for determining cardiac stroke volume of a subject comprising:
    sensing arterial blood pressure;
    converting the sensed arterial blood pressure to a pressure signal;
    determining the heart rate of the subject;
    determining the amplitude of a spectral component of the pressure signal for a frequency corresponding to a multiple of the heart rate;
    calculating an average value of the pressure signal; and
    calculating an estimate of the stroke volume as a function of the ratio of the amplitude of the spectral component and the average value of the pressure signal.

2. A method of claim 1, wherein sensing uses a blood pressure sensor, converting uses an analog-to-digital converter and further comprising outputting a parameter based on the estimate of stroke volume on a display.

3. A method of claim 1, wherein determining the amplitude of the spectral component includes using a Fourier transform.

4. A method of claim 3, wherein determining the heart rate includes using a Fourier transform.

5. A method of claim 4, wherein sensing arterial pressure is performed using a sensor placed in a peripheral artery.

6. A method for determining cardiac stroke volume of a subject comprising:
    sensing arterial blood pressure;
    converting the sensed arterial blood pressure to a pressure signal;
    detecting a maximum value and minimum value of the first time derivative of the pressure value during a measurement interval; and
    calculating an estimate of the stroke volume as a function of a magnitude of one of the maximum or minimum values,
    wherein the estimate of the stroke volume is proportionate to a standard deviation calculated using the magnitude of the maximum and minimum values.

7. A method of claim 6, wherein the estimate of the stroke volume is also proportionate to the magnitude of the maximum or minimum value.

8. A method of claim 7, wherein the estimate of the stroke volume is proportionate to the magnitude of both the maximum and minimum values.

9. A method of claim 6, wherein the standard deviation is calculated by dividing a sum of the magnitude of the maximum and minimum values by 3.

10. A method of claim 6, wherein detection of the maximum and minimum values is determined only between the beginning of a cardiac cycle and a dichrotic point.

11. A method of claim 6, wherein sensing uses a blood pressure sensor, converting uses an analog-to-digital converter and further comprising outputting a parameter based on the estimate of stroke volume on a display.

12. A method of claim 6, wherein a component of the estimate of the stroke volume includes the magnitude of one of the maximum or minimum values.

* * * * *